US008173568B2

United States Patent
Nishimura et al.

(10) Patent No.: US 8,173,568 B2
(45) Date of Patent: May 8, 2012

(54) PROCESS FOR PRODUCING TERTIARY AMINE

(75) Inventors: Toru Nishimura, Wakayama (JP); Shoji Hasegawa, Wakayama (JP); Osamu Tabata, Wakayama (JP); Kunio Matsui, Tochigi (JP)

(73) Assignee: Kao Corporation, Tokyo (JP)

( * ) Notice: Subject to any disclaimer, the term of this patent is extended or adjusted under 35 U.S.C. 154(b) by 252 days.

(21) Appl. No.: 10/574,907

(22) PCT Filed: Oct. 8, 2004

(86) PCT No.: PCT/JP2004/015313
§ 371 (c)(1),
(2), (4) Date: Apr. 25, 2007

(87) PCT Pub. No.: WO2005/035122
PCT Pub. Date: Apr. 21, 2005

(65) Prior Publication Data
US 2008/0004472 A1    Jan. 3, 2008

(30) Foreign Application Priority Data
Oct. 8, 2003 (JP) ................................ 2003-349740

(51) Int. Cl.
*B01J 31/06* (2006.01)
*B01J 35/00* (2006.01)
*C07C 209/16* (2006.01)

(52) U.S. Cl. ............ 502/100; 502/159; 502/344; 502/4; 564/479

(58) Field of Classification Search .................... 564/479
See application file for complete search history.

(56) References Cited

U.S. PATENT DOCUMENTS

| 4,177,323 | A | * | 12/1979 | Obi et al. ..................... 428/622 |
| 4,625,063 | A | * | 11/1986 | Yokota et al. ................. 564/480 |
| 4,631,263 | A | * | 12/1986 | Mizumoto et al. ............. 502/159 |
| 4,882,130 | A | * | 11/1989 | Asai et al. ..................... 422/310 |

FOREIGN PATENT DOCUMENTS

| EP | 0 281 417 A2 | | 9/1988 |
| EP | 1 254 715 A2 | | 11/2002 |
| JP | 55-149355 | * | 11/1980 |
| JP | 55-149355 A | | 11/1980 |
| JP | 61-17803 A | | 8/1986 |
| JP | 61-178039 A | | 8/1986 |

(Continued)

OTHER PUBLICATIONS

EP 04 77 3764, European Search Report, Aug. 30, 2010, 3 pages.

(Continued)

*Primary Examiner* — Melvin Mayes
*Assistant Examiner* — Yun Qian
(74) *Attorney, Agent, or Firm* — Birch, Stewart, Kolasch & Birch, LLP (57) ABSTRACT

The invention provides a method of using an alcohol and a primary or secondary amine as the starting material to produce the corresponding secondary amine easily at a high yield and a catalyst used therein. The invention relates to a film-type catalyst for production of a tertiary amine, which is used in producing a tertiary amine from an alcohol and a primary or secondary amine as the starting material, and a process for producing a tertiary amine, which includes reacting an alcohol with a primary or secondary amine in the presence of the film-type catalyst.

15 Claims, 3 Drawing Sheets

FOREIGN PATENT DOCUMENTS

| | | |
|---|---|---|
| JP | 3-4534 B2 | 1/1991 |
| JP | 3-34366 B2 | 5/1991 |
| JP | 6-211754 A | 8/1994 |
| JP | 7-112525 B2 | 12/1995 |
| JP | 9-271676 A | 10/1997 |
| JP | 2002-355554 A | 12/2002 |
| JP | 2003-135972 A | 5/2003 |
| JP | 2003-176255 A | 6/2003 |
| WO | WO 02/079128 A1 | 10/2002 |

OTHER PUBLICATIONS

European Office Action dated Jan. 12, 2011 for Application No. 04 773 764.8.

* cited by examiner

PROCESS FOR PRODUCING TERTIARY AMINE

FIELD OF THE INVENTION

The present invention relates to a film-type catalyst for producing a tertiary amine and a process for producing a tertiary amine by using the same.

BACKGROUND OF THE INVENTION

Fatty amines produced from tallow, coconut oil, palm oil etc, as the starting material are important intermediates in household and industrial fields. Particularly, fatty tertiary amines are converted into quarternary ammonium salts etc, and utilized in a wide variety of applications such as the field of fiber softening finishers, antistatic agents, rinse bases etc.

Conventionally, there is known a method wherein an alcohol and a primary or secondary amine are used as the starting material to produce the corresponding tertiary amine wherein a hydrogen atom bound to the nitrogen atom of the primary or secondary amine has been substituted by an alkyl group and/or an alkenyl group derived from the alcohol. The reaction mechanism is complicated, and not only mere hydrogenation reaction but also amine addition and dehydrogenation reactions are considered to produce simultaneously.

For example, JP-B 3-4534 discloses a method of obtaining an objective tertiary amine in high yield by using a catalyst based on copper/nickel/third component.

With respect to the form of a catalyst used in a fixed-bed system, a molded catalyst in the form of pellets, noodles or tablets have been conventionally well known. Powdery substance having a catalyst activity is molded in the above-mentioned formed by a method such as compression or extrusion to provide a molded product with a structure having numberless pores in it to satisfy both bulk form and large surface area. Such molded catalyst is disclosed in, for example, JP-A 6-211754.

Another form of the catalyst used in the fixed-bed system, a monolithic catalyst is known. For example, JP-A 2003-176255 discloses a reactor having a catalyst metal adhering to the surface of a monolithic.

In the monolithic or honeycomb catalyst technology, technical disclosure on pore structures of the catalysts is found. For example, JP-A 2002-355554 discloses a coated monolithic substrate containing a wash coat formed from a solution forming a furfuryl alcohol-containing polymer or from a pre-polymer containing a furfuryl alcohol polymerizable unit and a monolithic catalyst having a catalyst metal deposited thereon.

In the monolithic or honeycomb catalyst technology, many examinations have been made for supporting a catalyst active substance on a substance by coating, particularly in the field of photocatalyst in recent years. For example, JP-A 9-271576 discloses a method of supporting photocatalyst particles, which includes applying a dispersion of titanium oxide particles in water or in a binder solution onto a substance, then drying it, further applying a binder solution onto the resulting catalyst layer and drying it.

JP-A 2003-135972 discloses a porous thin-film photocatalyst produced by coating a substance with a coating solution containing a photocatalyst active material and/or its precursor and a subliming agent then subliming the subliming agent thereby forming pores.

A SUMMARY OF THE INVENTION

The present invention provides a film-type catalyst for producing a tertiary amine, which is used in producing a tertiary amine from an alcohol and a primary or secondary amine as the starting material and a process for producing a tertiary amine, which includes reacting an alcohol with a primary or secondary amine in the presence of the film-type catalyst. The present invention also provides use of the film-type catalyst in producing a tertiary amine by reacting an alcohol with a primary or secondary amine.

DETAILED DESCRIPTION OF THE INVENTION

Even if the catalyst in JP-B 3-4534 supra is used, techniques such as agitation and gas bubbling are necessary for effectively mixing reactants with the catalyst when a process of suspension-bed system using the catalyst in a powdery form is used. In the process of suspension-bed system, there is the problem of complex facilities and operation such as necessity for separation of the product from the catalyst by filtration.

On the other hand, a fixed-bed system can be mentioned as a process neither requiring the operation of mixing the catalyst by agitation, gas bubbling etc. nor separating the catalyst by filtration.

When the molded catalyst in JP-A 6-211754 supra is used in this reaction to obtain the product in a high rate of reaction, quite a few undesirable byproducts are generated. The undesirable byproducts include not only wax or a aldol condensates generated by side reactions of an alcohol as the starting material but also tertiary amines produced as byproducts from ammonia, primary amine or secondary amine generated by disproportionation of a primary or secondary amine (as the starting material). Improvements in techniques for selective reaction to prevent formation of these byproducts have been extensively examined, but it has been difficult to carry out this reaction highly selectively by an easy process. That is, high productivity and high yield are hardly simultaneously satisfied.

JP-A 2003-176255 supra has noted that because in hydrogenation reaction between a reactant gas and a reactant liquid, pressure drop in the reactor is small so that the velocity of the gas and liquid can be increased, the reactor is advantageous in promotion of mass transfer over a conventional reactor loaded with a fixed bed. However, the reaction specified therein is a reaction by simple mechanism only such as hydrogenation, although the reaction of a nitrogen atom-containing compound is intended. Other examples disclosed therein are also limited in use to mainly hydrogenation reaction, and there is no example wherein the reaction is applied to a reacted having extremely complex mechanism, such as a reaction of an alcohol with a primary or secondary amine as the starting material to give the corresponding tertiary amine in higher yield.

JP-A 2002-355554 supra describes that both the coated monolithic substrate and the monolithic catalyst have a surface area in the range of 0.1 to 25 m²/g thereby attaining the reaction activity and the retaining properties of a catalyst metal. However, the catalyst should be produced by complicated steps such as a step of depositing a wash coat and a step of supporting a catalyst metal, and the complicated steps make it difficult for the catalyst to regulate the pore structure and surface physical properties, so the reaction activity of the catalyst ids hardly exhibited.

In JP-A 9-271676 supra, a catalyst film containing catalyst particles is obtained by first coating/drying, but there is worry about troubles in the production process, such as low strength and easy release. In a second coating/drying step, the catalyst film obtained by the first coating/drying step is coated further with a binder solution, and thus the adhesion in the interface between the catalyst film and the binder cannot be sufficiently exhibited. If the binder is used in a large amount to increase adhesiveness, there are problems such as low degree of the catalyst resulting low catalyst activity, etc.

The diameters of pores formed by eliminating a sublimating agent on JP-A 2003-135972 supra are greater than the thickness of the catalyst layer to permit the substance to be topically exposed, thus causing problematic detachment of the catalyst layer from the interface and making stable formation of a uniform film difficult.

With respect to the monolithic or honeycomb catalyst technology described above, the catalyst activity, the retaining properties of the catalyst active substance, or suppression of the release thereof have been examined as described above. In the method of fixing a powdery catalyst via a binder onto a substrate, among the methods mentioned above, there is a problem that the coverage of the surface of the powdery catalyst with the binder causes a reduction in the reaction rate, while when the amount of the binder is too reduced, the retaining properties of the powdery catalyst are deteriorated and release of the coating easily occurs. In the method of forming a catalyst active substance on a substrate, calcination of an active precursor to convert it into an active substance is essential, so that complicated operation is necessary to perform and preparation conditions should be examined in further detail in order to endow the catalyst active substance with suitable catalyst activity and selectivity with good balance.

The present invention provides a process for using an alcohol and a primary or secondary amine as the starting material to produce the corresponding tertiary amine easily at a high yield and a catalyst used therein. For achieving the invention, the present invention provides a film-type catalyst having a sufficient catalyst activity and being hardly released, and a process for producing the film-type catalyst.

In the present invention, the starting alcohol used in the process for producing a tertiary amine according to the present invention is preferably a linear or branched C8 to C36 saturated or unsaturated aliphatic alcohol. Specific examples includes octyl alcohol, lauryl alcohol, myristyl alcohol, stearyl alcohol thereof, Ziegler alcohol obtain by the Ziegler process, an oxo alcohol obtained by an oxo process, and Guerbet alcohol.

The starting primary or secondary amine used in the process for producing a tertiary amine according to the present invention includes an aliphatic primary or secondary amine, and examples thereof includes methylamine, dimethylamine, ethylamine, diethylamine, dodecylamine, didodecylamine etc.

The alcohol and primary or secondary amine used as the starting materials give the corresponding tertiary amine wherein a hydrogen atom bound to the nitrogen atom of the primary or secondary amine has been substituted by an alkyl group and/or an alkenyl group derived from the alcohol. For example, the tertiary amine obtained from lauryl alcohol and dimethylamine is N-dodecyl-N,N-dimethylamine which is distinguished from tertiary amine byproducts N,N-didodecyl-N-methylamine and N,N,N-tridodecylamine formed by reaction concerned with methylamine and ammonia generated by disproportionation of dimethylamine.

The film-type catalyst used in the present invention is different from a conventional catalyst of unordered packing type having several millimeters or thereabout, and refers to a catalyst in the form of a thin film having a thickness of 500 μm or less. The process of transferring the reactants and the product in the inside of the catalyst is governed by diffusion, and the distance is reduced to 500 μm or less, whereby the mass transfer between the inside and outside of the catalyst can be promoted thereby effectively utilizing the whole of the catalyst and simultaneously suppressing the excessive reaction of the intermediate reaction product in the inside of the catalyst. As will be evident from the results in the examples described later, the thickness of the film-type catalyst is particularly preferably 100 μm or less, more preferably 50 μm or less, in order to significantly increased the reaction activity per catalyst unit weight. The lower limit of the thickness is preferably 0.01 μm or more, still more preferably 1 μm or more, in order to secure the strength of the catalyst layer and attain durability of the strength thereof.

The structure of the film-type catalyst includes various structures depending on the shape of a reactor. For example, a catalyst coating layer formed on a wall in a tube, a catalyst formed in a tube in the form if a thin plate by which the tube is divided in an axial direction into a plurality of flow paths, etc, are mentioned and can be used preferably in a tubular circulating reactor. The catalyst may be a catalyst coating layer or the like formed on the surface of an open fin-shaped flat plate arranged in tank and can be preferably used in a tank reactor. In any cases, the catalyst is preferably structured such that supply of the reactants to the catalyst and recovery of the product from the catalyst can easily occur. The surface of the catalyst where supply of the reactants to the catalyst and recovery of the product from the catalyst occur is desirably as large as possible for efficient progress of the reaction. For achieving the above requirement, it is preferable to use the film-shaped catalyst arranged in a structure having assembled tubes each having an inner diameter of several millimeters to several ten millimeters or in the inner wall of a honeycomb structure having several ten to several hundred cells per square inch.

For forming the film-type catalyst in the various structures, there is for example a method of forming the catalyst active substance itself into a honeycomb structure, but from the viewpoint of satisfying both a thin catalyst layer and high mechanical strength, the film-type catalyst is preferably fixed on the surface of a substance. The film-type catalyst is preferably a metal foil. There is for example a method wherein a coating layer containing the catalyst active substance is formed on the surface of a metallic or other rigid, tubular, planar or honeycomb substance to produce the film-type catalyst. As the coating method, it is possible to use conventionally known methods including not only physical deposition such as sputtering, chemical deposition, and dipping into a solution, but also various costing methods with a binder, such as blade coating, spray coating, dip coating, spin coating, gravure coating and die coating.

The active substance constituting the film-type catalyst is not particularly limited and may be a known active substance, and generally a metal such as copper can be preferably used, and a metal containing copper is more preferably used. For example, use is made of Cu alone or a metal containing 2 components, that is, Cu and a transition metal element such as Cr, Co, Ni, Fe or Mn, preferably a metal containing Cu and Ni. Further, a metal containing 3 components or more is also preferably used. Further, the metal supported on a carrier such as silica, alumina, titania or zeolite can also be used.

The film-type catalyst can contain a binder which does not act as an active substance but fixes the active substance to form the film-type catalyst. The binder includes high-molecular or inorganic compounds which are durable to the reaction environment, do not adversely affect the reaction system and have not only a property of binding particles of the active substance together or binding the active substance to the surface of a substance but also properties such as chemical resistance and heat resistance. Example of the binder include cellulose resin such as carboxymethyl cellulose and hydroxyethyl cellulose, fluorine-based resin such as poly(tetrafluoroethylene) and poly(vinylidene fluoride), high-molecular compounds such as urethane resin, epoxy resin, polyester resin, phenol resin, melamine resin, silicone resin, polyvinyl alcohol, polyimide resin and polyimide amide resin, and sol of inorganic compound such as silica and alumina.

The internal structure of the film-type catalyst depends significantly on the type of the active substance constituting the catalyst and on the method if preparing the catalyst, and may form a dense continuous phase or may be porous. For example, when the catalyst is a thin film formed in the surface of a substrate by sputtering and chemical vapor deposition, the catalyst can have a dense continuous phase, while when the powdery active substance is used to form a thin on the surface of a substrate by wet or dry coating, the catalyst can be porous.

As the method of producing the film-type catalyst, it is particularly preferable to use a method of forming, on a substrate, a coating containing a powdery catalyst active substrate and a binder for fixing it. Particularly, in the film-type catalyst obtained by forming, on a substrate, a coating film containing a powdery catalyst together with synthetic resin used as a binder in the method of producing the same, the compounding ratio of the powdery catalyst to the synthetic resin can be regulated in such a suitable range as to control the degree of exposure of the powdery catalyst and the binding strength among the catalyst powders and the binding strength between the substrate and the catalyst powders.

In the film making method, the compounding ratio is preferably a ratio of 20 to 80 parts by weight of the synthetic resin to 100 parts by weight of the powdery catalyst. The film-type catalyst exhibiting the reaction activity particularly effective as a film-type catalyst and hardly releasing its coating can be obtained by further controlling the pore volume per unit area of the substrate in the range of 0.5 to 30 mL/m$^2$.

In the internal structure of the film-type catalyst obtained by the above film making method, the surface of the powdery catalyst is coated wholly or partially with the synthetic resin, and the powdery catalyst particles are bound to one another via the synthetic resin, and a large number of the powdery catalyst particles are deposited in the direction of thickness. A large number of such deposited powdery catalyst particles form a 3-dimensional network structure via the synthetic resin, and air layers lie scattered in spaces among the powdery catalyst particles, and preferably the synthetic resin itself also has a pore structure. The film-type catalyst can have a gradient structure wherein the ratio of the powdery catalyst to the synthetic resin is changed in the direction of thickness, or the film-type catalyst layer may include two or more catalyst layers different in the ratio of the powdery catalyst to the synthetic resin therein two or more catalyst layers different in pore structure.

In the film-type catalyst obtained by the film making method described above, the synthetic resin is contained preferably in an amount of 20 to 80 parts by weight relative to 100 parts by weight of the powdery catalyst, whereby the catalyst activity, or the binding strength among the powdery catalyst particles or between the powdery catalyst and the substrate, can be effectively exhibited. In the film-type catalyst, the pore volume of the catalyst layer per unit surface area of the substrate is desirably 0.5 to 30 mL/m$^2$, preferably 1 to 20 mL/m$^2$, more preferably 1 to 4 mL/m$^2$. When the pore volume is not less than 0.5 mL/m$^2$, the diffusion rate in the catalyst layer is increased, and upon application of the film-type catalyst to the reaction process, a high reaction rate can be obtained. When the pore volume is too large, the catalyst layer is made porous at high degree, the binding strength among the powdery catalyst particles and/or between the powdery catalyst and the substrate is reduced thus reducing the mechanical strength of the catalyst layer, while when the pore volume is 30 mL/m$^2$ or less, the porosity of the catalyst layer becomes suitable, and the adhesion among the powdery catalyst particles and/or between the powdery catalyst and the substrate is increased. As a result, the mechanical strength of the catalyst layer is increased and simultaneously the mass transfer of the reactants and products can be kept in an excellent state.

The pore structure of the film-type catalyst obtained by the film making method is determined in a step of eliminating volatile components and in step of forming a twined structure of synthetic resin after coating a substrate with a coating containing the synthetic resin preferably in the range of 20 to 80 parts by weight relative to 100 parts by weight of the powdery catalyst. When the synthetic resin is thermosetting resin, the pore structure is determined at the time of forming a crosslinked structure (network structure) formed by progress of curing/crosslinking reaction, in addition to the step of eliminating volatile components. When the reaction is accomPanied by condensation reaction, the pore structure is also influenced by the step of eliminating the condensation product. As a result of eager study, it was found that when the pore volume per unit surface area if the substrate, as an indicator characterizing the pore structure formed, is 0.5 to 30 mL/m$^2$, sufficient reaction rate of the film-type catalyst in the reaction process and the retaining properties of the powdery catalyst can be preferably maintained.

The powdery catalyst used in the film making method is preferably a catalyst whose performance has been established for the suspension-bed process. In this case, the development time for film-type catalyst, as comPared with the method of converting a catalyst active substance precursor fixed on a substrate into a catalyst active substance by treatment such as calcination, can be shortened because reaction characteristics in the reaction process can be secured. The production process can be simplified because the complicated production process for exhibiting the reaction activity, such as calcination treatment, is not necessary.

The powdery catalyst used in film making method is preferably the one having particle diameters, preferably with sharp distribution, of 0.01 to 500 μm, preferably 0.1 to 100 μm, more preferably 0.5 to 50 μm, in terms of average particles diameter, and a specific surface area of 0.1 to 5000 m$^2$/g, preferably 1 to 200 m$^2$/g, more preferably 10 to 100 m$^2$/g, as determined by the BET method. For example, the powdery catalyst can be prepared by using the following catalyst carrier and catalyst active substance precursor.

The catalyst carrier for preparing the powdery catalyst used in the film making method includes carriers such as active carbon, alumina, silica, zeolite, titania, silica-alumina and diatomaceous earth, and one or more carriers selected there from can be preferably used, More preferably, a porous carrier having a large surface area can be used, and further a catalyst carrier such as molecular sieves can be used.

The catalyst active substance precursor for preparing the powdery catalyst used in the film making method includes sulfates, nitrates, ammonium complex salts, acetates, oxalates, acetylacetonates and chlorides of metals such as the fourth transition metal elements in the periodic table such as Cu, Ni, Zn, Co, Fe and Cr and then platinum elements such as Pt, Pd and Ru.

As the method wherein the powdery catalyst used in the film making method is prepared from the catalyst carrier and the catalyst active substance precursor, it is possible to employ conventional known methods such as a dipping method, co-dipping method, co-precipitation method and ion exchange method.

The synthetic resin used in the film making method is preferably a resin excellent in binding properties among the powdery catalyst particles and between the powdery catalyst and the surface of the substrate, being durable to the reaction environment and mot adversely affecting the reaction system. The synthetic resins used include various thermoplastic resins and thermosetting resin, for example the high-molecular compounds mentioned in the above examples of the binder, and are preferably those capable of attaining high-molecular weights through crosslinking reaction of the synthetic resins with a curing agent. Particularly, thermosetting resins such as phenol resin, furan and epoxy resin are preferable, and more preferably thermosetting resin undergoing condensation reaction upon curing can be used. When such thermosetting resin is used, the crosslinking density is increased by the curing reaction, whereby the strength of the resulting coating and binding properties are improved and the catalyst coating is made further porous by condensation reaction thereby enabling sufficient utilization of the catalyst activity of the powdery catalyst.

When the film-type catalyst is produced by the film making method, a combination of the powdery catalyst of copper/nickel/ruthenium ternary system and phenol resin can be mentioned as one example of the combination of the powdery catalyst and the synthetic resin.

The compounding ratio of the powdery catalyst to the synthetic resin in the film making method is preferably a ratio of 20 to 80 parts by weight, more preferably 30 to 70 parts by weight, still more preferably 40 to 60 parts by weight of the synthetic resin to 100 parts by weight of the powdery catalyst. By regulating the compounding ratio of the powdery catalyst to the synthetic resin in the range mentioned above, the degree of exposure of the powdery catalyst can be controlled to effectively utilize its catalyst activity, and release of the coating can be prevented. When the amount of the synthetic resin incorporated is 80 parts by weight or less, the thickness of the synthetic resin covering the surface of the powdery catalyst or the degree of coverage with the synthetic resin is made suitable, and the catalyst activity of the powdery catalyst can be sufficiently demonstrated to exhibit a high catalyst activity. When the amount of the synthetic resin incorporated is 20 parts by weight or more, the catalyst activity is sufficiently demonstrated, and the binding strength among the powdery catalyst particles or between the powdery catalyst and the substrate can be improved to reduce the amount of the catalyst layer released or partially removed during the process of producing the film-type catalyst and during the reaction operation.

In the film making method, a solvent as a third component in addition to the powdery catalyst and synthetic resin can be preferably used in order to prepare a coating. The solvent may be any solvent which does not adversely affect the reaction activity of the powdery catalyst, and depending on the type of the synthetic resin used, the solvent can be selected from various kinds of water-soluble or water insoluble solvents, and the pore structure of the film-type catalyst can be controlled by selection of the solvent. Example of the solvent include water; alcohols such as methyl alcohol, ethyl alcohol, isopropyl alcohol, butyl alcohol and alkyl alcohol; glycols and derivatives thereof such as ethylene glycol, polyethylene glycol, polypropylene glycol, diethylene glycol monoethyl ether, polypropylene glycol monoethyl ether, polyethylene glycol monoallyl ether and polypropylene glycol monoally ether; glycerol and derivatives thereof such as tetrahydrofuran and dioxane; ketones such as methyl ethyl ketone, methyl isobutyl ketone and acetone; hydrocarbons such as liquid paraffin, decane, decene, methyl naphthalene, decalin, kerosine, diphenyl methane, toluene, dimethyl benzene, ethyl benzene, diethyl benzene, propyl benzene, cyclohexane and partially hydrogenated triphenyl; silicone oils such as polydimethyl siloxane, partially octyl-substituted polydimethyl siloxane, partially phenyl-substituted polydimethyl siloxane and fluorosilicone oil; halogenated hydrocarbons such as chlorobenzene, dichlorobenzene, bromobenzene, dichlorodiphenyl and chlorodiphenyl methane; fluoride such as DAILROL (DAIKIN INDUSTRIES, Ltd.) and DEMNUM (DAIKIN INDUSTRIES, Ltd.), ester compounds such as ethyl benzoate, octyl benzoate, dioctyl phthalate, trioctyl trimellitate, dibutyl sebacate, ethyl (meth) acrylate, butyl (meth) acrylate and dodecyl (meth) acrylate; and besides dimethylformamide, N-methyl-pyrrolidone, acetonitrile and ethyl acetate. The solvent is preferably the one having an excellent ability to solubilize the synthetic resin and may be a mixed solvent of two or more solvents. By selecting a solvents adapted to the synthetic resin selected, the pore structure can be regulated.

In the film making method, preparation of a coating containing the powdery catalyst and synthetic resin can be carried out in a usual manner, and the coating can be prepared by using suitably selected steps such as a kneading step, a dissolving step, a dispersing step with a sand mill or the like, and a filtering step. In the dispersing step, a paint shaker, a basket mill, a grain mill, DYNO-mill, an or the like id used to form the coating.

In preparation of the coating in the film coating method, it is known that by selecting suitable conditions such as dispersing time, the reaction characteristics of the finally obtained film-type catalyst and the strength of the coating (catalyst layer) can be improved and the release of the coating (film-type catalyst layer or powdery catalyst) can be prevented. Particularly, the characteristics can be controlled in connection with the degree of the coating. The criteria of the degree of dispersion of the coating can be numerically expressed by means such as glossiness, a grindometer, viscosity and rheological characteristics. In the dispersing step, dispersing treatment can be carried out efficiently when the solids contents of the coating is high, and the solids content so preferably 10 to 80 wt %, more preferably 20 to 70 wt %, more preferably 25 to 65 wt %. The viscosity of the coating is preferably 5 to 10,000 mPa·s, more preferably 20 to 5000 mPa·s, still more preferably 50 to 1000 mPa·s. For example, the powdery catalyst, synthetic resin and solvent are added to a stainless steel vat, mixed and stirred until visually recognizable mass of the powdery catalyst disappears, and then the mixture is transferred into a vessel of a basket mill and then mixed and dispersed at a predetermined revolution number and aggregates or foreign matter are removed by precision filtration, whereby the objective coating can be prepared. In the dispersing treatment for preparing the coating, the starting materials when introduced in an amount of 10,000 g (total amount of the powdery catalyst, synthetic resin and solvent) for example into a mixing tank of a 20-L basket mill are stirred desirably at 800 to 3000 rpm for 30 to 600 minutes. The dispersing treatment, when judged with glossiness, is conducted desirably until, for example, evaluated glossiness confirmed with time reaches the maximum. The dispersing treatment, when judged with a grindometer, is conducted desirably until secondary aggregation has been reduced in judgment based on the primary particle diameter of the powdery catalyst.

In preparing the coating by the film making method, the coating can be compounded with a surfactant as a dispersing agent, a coupling agent, inorganic particles and fibrous materials as aggregate, and a high-boiling point solvent as an agent for siding in increasing porosity, in addition to the powdery catalyst synthetic resin and solvent. The coupling agent had an effect of improving physical properties by molecular crosslinkage in the interface between the inorganic filler and the organic polymer matrix. As the coupling agent, it is possible to use a coupling agent generally known as silane coupling agent, titanate-based coupling agent and aluminate-based coupling agent, and a combination of a plurality of coupling agents can be incorporated and may be used after dilution with a compatible organic solvent for concentration regulation. As the fibrous materials, organic or inorganic fibers are used. The organic fibers include polyamide fibers such as nylon 66, aramid fiber, polyvinyl alcohol-based fiber, polyester-based polyethylene terephthalate, polybutlene terephthalate fiber, polyarylate fiber, polyvinylidene chloride-based fiber, polyvinyl chloride-based fiber, polyacrylonitrile-based fiber, and polyolefin-based polyethylene and polypropylene fibers. The organic fibers include organic regenerated fibers such as cellulose-based rayon, acetate etc. The inorganic fibers used include glass fiber, carbon fiber, active carbon fiber, ceramic fiber and asbestos, and the mechanical strength of the catalyst coating can be improved by the effect of the aggregate.

The substrate used in the film making method may be a substrate made of a durable material not adversely affecting the reaction system in which the film-type catalyst of the present invention is used. The substrate can be selected suitably depending on the shape of the objective film-type catalyst and can be a planar, tubular, honeycomb or monolithic substrate.

As the planar substrate used in the film making method, a substrate having suitable processability enables shaping of the catalyst formed into a film and can be preferably used. Examples of the planar substrate include a copper foil, stainless steel foil, aluminum foil etc. The copper foil and stainless steel foil can be preferably used from the viewpoint of processability and corrosion resistance.

The honeycomb or monolithic substrate used in the film making method includes, but are not limited to, substrates containing cordierite, carbon composite, mullite, clay, magnesia, talc, zirconia, spinel, alumina, silica, ceria, titania, tungsten, chrome, stainless steel, copper, alumina and nickel. The term "honeycomb" refers to a shape having a large number of assembled cells, forming a bees' nest structure divided with thin walls. The honeycomb structure has a large surface area per unit volume, and is thus preferably used in the substrate constituting the film-type catalyst. Each cell is preferably in the form of an equilateral triangle, an equilateral pentagon or an equilateral hexagon in which cells can be assembled with no gap, and the substrate can also be constituted by combing section-shape cells or polygonal cells. For example, an integrally molded structure formed by extrusion molding, or a substrate formed by stacking, with a flat material, several corrugated layers obtained by shaping flat materials, can also be preferably used as the honeycomb substrate.

The surface of the substrate used in the film making method is preferably subjected to roughing treatment or coupling treatment from the viewpoint of improving the adhesion thereof to the catalyst layer. In this coupling treatment, the above-mentioned coupling agent can be used, and preferably the same coupling agent as used in preparing the coating can be used.

Specifically, the film making method includes a method of applying the coating containing the powdery catalyst onto the surface of the substrate to form a film thereon. This film making method may be a conventional method including various coating methods such as blade coating, roll coating, knife coating, bar coating, spray coating, dip coating, spin coating, comma coating, kiss-roll coating, gravure coating and die coating. The pore structure is regulated at the time of eliminating volatile components such as solvent from the catalyst layer formed as a film, and thus the solids content of the coating in making the film influence formation of the pore structure. The solids content of the coating in forming the film is preferably in the range of 10 to 80 wt %, more preferably 20 to 70 wt %, still more preferably 25 to 65 wt %. The viscosity of the coating in forming the film is selected in a preferable range depending on each of the coating methods mentioned above, and is preferably 5 to 10,000 mPa·s, more preferably 20 to 5000 mPa·s, still more preferably 50 to 1000 mPa·s.

In the film making method by coating, the drying and curing treatment can be carried out after the coating containing the powdery catalyst is applied onto the surface of the substrate. The drying and curing treatment step is carried out preferably in an atmosphere such as heated air, water vapor, nitrogen or an inert gas such argon, or by using various means such as a method of spraying such heated medium, a method of utilizing radiation heat infrared rays, and a heating system using an induction current by an electromagnetic wave. A combination of these methods or a method of natural drying (air-drying) at ordinary temperatures can also be used. The volatile components eliminated in this step include cured reaction products and unreacted monomer components in addition to the solvent.

The drying conditions in the film making method by coating should be regulated depending on the physical properties of the synthetic resin and volatile components based on the solvent contained in the coating, and the pore structure (pore volume) of the film-type catalyst can be regulated by selecting a suitable solvent and setting drying and curing conditions. That is, the pore structure is determined not only at the stage of evaporation of volatile components such as solvent from the coating, but also at the time of formation of a crosslinked structure (network structure) formed by progress of the curing and crosslinking reaction and also at the stage of elimination of condensation products when the reaction is accompanied by condensation reaction. Generally, the components are evaporated more rapidly from the catalyst layer and the pore structure (pore diameter, volume) is increased as the temperature is raised and the air flow is increased in the heating treatment with hot air. The pore structure is decreased as the temperature is reduced and air flow is decreased.

In the film-forming method by coating, the drying and curing treatment can make use of a method and conditions not adversely affecting the inherent activity of the powdery catalyst, in order to regulate the pore volume in the range of 0.5 to 30 mL/m$^2$. With respect to drying and curing conditions with hot air for obtaining the objective film-type catalyst, the drying and curing treatment is carried out desirably at a temperature of typically 50 to 400° C., preferably 70 to 250° C., more preferably 80 to 150° C., at an air flow of preferably 0.5 to 30 m/sec., more preferably 1 to 20 m/sec., for a period of preferably 1 or more seconds, more preferably 10 minutes or more, still more preferably 30 minutes or more.

In the film making method by coating, it is preferable that the coating is dried immediately after application onto the substrate, wherein the pore structure of the coating can be controlled by regulating the drying conditions. Accordingly, the time of form formation of the catalyst layer on the substrate to elimination of volatile components such as solvent is desirably shorter, preferably within 2 hours, more preferably within 30 minutes.

When thermosetting resin is used as the synthetic resin or the plasticity of the synthetic resin is reduced by crosslinking reaction in the film making method by coating it is desired that the coating film obtained by coating and drying is subjected to shaping while it remains uncured (prepolymer state), followed by final heating treatment to form the film-type catalyst.

In the film making method involving the final heating treatment, the drying treatment carried out before the final heating treatment is finished while the synthetic resin remains unreacted. Desirably, the synthetic resin is partially cured to such a degree that it can be handled at the time of shaping, and the retaining properties and mechanical strength of the catalyst layer are improved as compared with those at the time of coating, and the volatilize components such as solvents may remain in the order of several % in the coating film. Hot-air drying before the final heating treatment for obtaining the objective film-type catalyst is carried out desirably at a temperature of typically 50 to 400° C., preferably 70 to 250° C., more preferably 80 to 150° C., at an air flow of preferably 0.5 to 30 m/sec., more preferably 1 to 20 m/sec., for a period of preferably 0.5 to 300 seconds, more preferably 1 to 100 seconds.

In the film making method involving the final heating treatment, the coating layer is shaped before it is completely cured, whereby the coating layer can follow the shape of the elastically deformed substrate to improve shaping processability. After the processing is finished, the coating layer can be completely cured by heating treatment thereby fixing the crosslinked structure of the catalyst layer in the final stage of the production process, relieving the residual stress of the catalyst layer and reducing release of the catalyst layer or the powdery catalyst from the film-type catalyst. When thermoplastic resin is contained as the synthetic resin, it is desired that the coating film obtained by coating and drying is subjected to shaping and then to final heating. When thermoplastic resin is contained in the coating film, residual stress may be generated in the coating upon elastic deformation of the substrate subjected to shaping, thus adversely affecting the retaining properties of the coating film. Accordingly, the stress can be relieved by the final heating treatment, and simultaneously the twisted structure of the thermoplastic resin is reinforced thereby reducing the release of the catalyst layer or the powdery catalyst from the film-type catalyst. The final heating treatment conditions vary depending on the type of the synthetic resin, but in the present invention, this treatment is carried out desirably at a temperature of preferably 80 to 400° C., more preferably 100 to 200° C., for a period of preferably 5 to 600 minutes, more preferably 10 to 100 minutes. A reactor loaded with the film-type catalyst can be in various forms including those known in the art. As described above, a tubular circulating reactor and a tank reactor can be mentioned. In the case of the tubular reactor, the reaction can proceed continuously or batchwise by circulating the reactants once or by feeding the reactants through circulation in a circulating system wherein the reactants are fed to the film-type catalyst in the tubular reactor while the product is continuously recovered therefrom. In the case of the tank reactor, the reactants are circulated in the tank, to feed them to the film-type catalyst in the tank, and the reaction can proceed continuously or batchwise.

The conditions where an alcohol is reacted with a primary or secondary amine in the presence of the film-type catalyst vary depending on the reactants, the product and the type of the catalyst. The reactants may be present in a gaseous or liquid phase. When a gaseous phase is present in the reaction system, the reaction of the reactants in an atmosphere of hydrogen, nitrogen and/or a rare gas is preferable for maintaining the catalyst activity. When the alcohol and the primary or secondary amine are present in different phases respectively in a reaction system of gaseous/liquid two phases, promotion of mass transfer between the two phases by gas bubbling in the liquid is desired. The mass transfer can also be promoted by feeding the reactants in a gaseous/liquid mixed phase to the reaction field where a thin flow path having a diameter of several millimeters or less is formed from the film-type catalyst. The pressure in the system is desirably not significantly higher than normal pressure. Although the reaction temperature varies depending on the type of the catalyst, the reaction is preferably conducted at a temperature of 150 to 300° C. Water produced as a byproduct in the reaction is discharged from the reaction system, whereby progress of the reaction can be promoted and the catalyst activity can be maintained.

According to the method of the present invention, an alcohol and a primary or secondary amine can be used as the starting material to produce the corresponding tertiary amine in high yield by an easy process.

According to the method of the present invention, the objective tertiary amine can be obtained in high yield by an easy process not necessitating any special mixing operation or any operation of separating the catalyst. The film-type catalyst of the present invention, that is, the film-type catalyst obtained by the production process of the present invention has a sufficient catalyst activity and hardly releases the catalyst.

EXAMPLES

The following examples describe the practice of the present invention. The example are set forth for mere illustration of the present invention and are not intended to limit the present invention.

In the Examples and Comparative Examples below, a circulating fixed-bed reaction apparatus shown in FIG. 1, a bubbling tank reaction apparatus in FIG. 2, and an agitating tank reaction apparatus in FIG. 3 were used.

Figure 1:
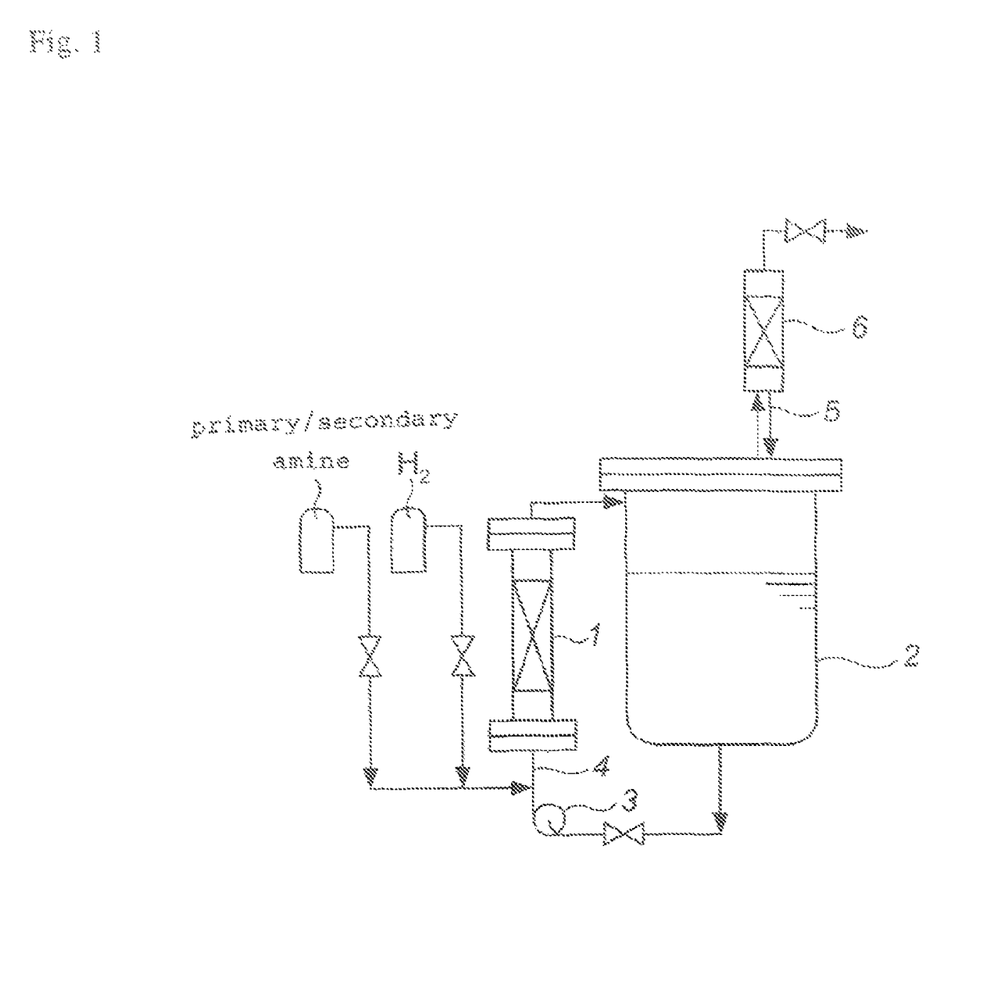
FIG. 1 is a schematic view of a circulating fixed-bed reaction apparatus used in Example 1 and Comparative Example 1. In the figure, 1 is a reaction column, 2 is a buffer tank, 3 is a pump, 4 is a conduit, 5 is a conduit, and 6 is a condenser.

In FIG. 1, the reaction column 1 is an vertical cylindrical fixed-bed reactor loaded with the catalyst and capable of regulating the temperature by external heating. The buffer tank 2 is a tank for storing liquid reactants and/or a product mixture, which is circulated by a pump 3 between the buffer tank 2 and the reaction column 1. Reactants and/or a product mixture, and a gaseous primary or secondary amine and a hydrogen gas, are continuously through conduit 4 from the lower end of the reaction column 1, while an unreacted material and/or a product mixture and a hydrogen gas are continuously recovered from the upper end and introduced into the buffer tank 2. An unreacted gaseous primary or secondary amine and water are continuously discharged through conduit 5. In the components discharged from the conduit 5, a mist of components such as the alcohol and/or the formed tertiary amine may be contained in addition to the components described above, and these components are liquefied by condenser 6 and returned to the buffer tank 2, and the remaining gaseous components are discharged outside of the system. The inside of the reaction system is kept at almost normal pressures.

Figure 2:
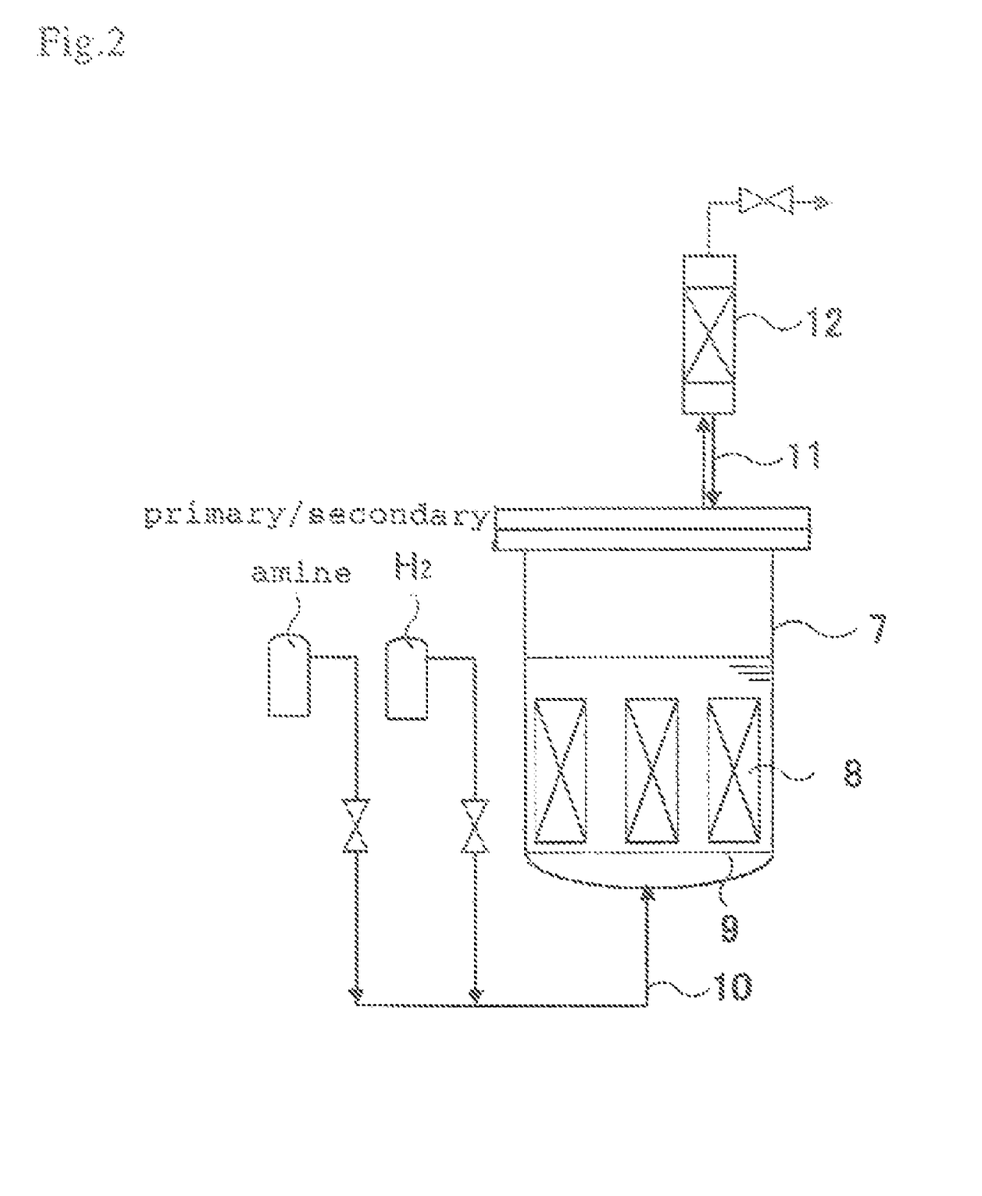
FIG. 2 is a schematic view of a bubbling tank reaction apparatus used in Example 2, in the figure, 7 is a reaction tank, 8 is a film-type catalyst, 9 is a filter plate, 10 is a conduit, 11 is a conduit, and 12 is a condenser.

In FIG. 2 the reaction tank 7 is a bubbling tank fixed-bed reactor loaded with the film-type catalyst 8. Reactants and/or a product mixture were accommodated in the reaction tank 7 and the temperature can be regulated by external heating. A gaseous primary or secondary amine and a hydrogen gas are fed from conduit 10 through a glass filter plate (2G) 9 arranged at the bottom of the reaction tank 7. An unreacted gaseous primary or secondary amine and water are continuously discharged through conduit 11. In the components discharged from the conduit 11, a vapor mist of components such as the alcohol and/or the formed tertiary amine may be contained in addition to the components described above, and these components are liquefied by condenser 12 and returned to the buffer tank 7, and the remaining gaseous components are discharged outside of the system. The inside of the reaction system is kept at almost normal pressures.

Figure 3:
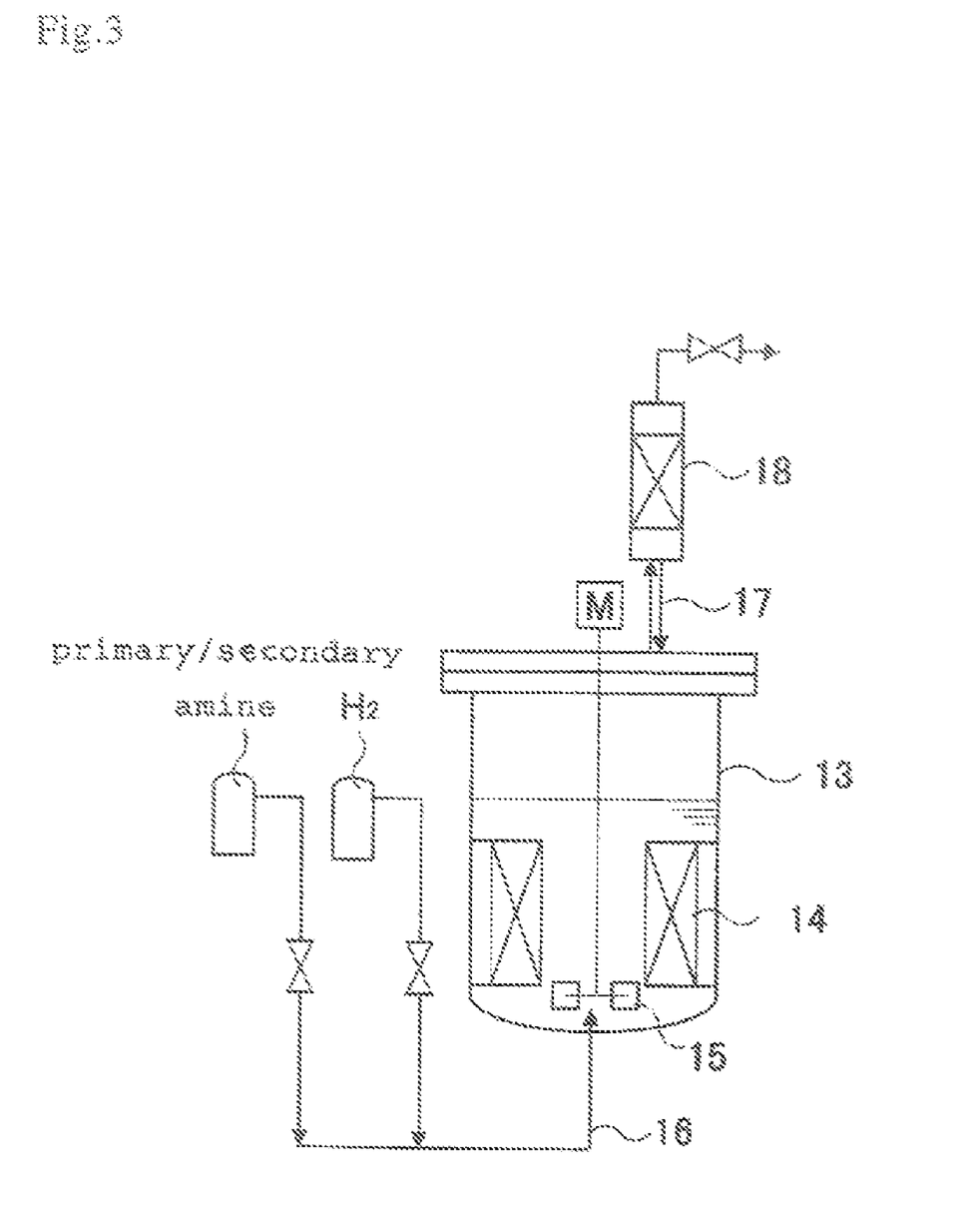
FIG. 3 is schematic view of a stirring tank reaction apparatus used in Example 3. In the figure, 13 is a reaction tank, 14 is a square pillar film-type catalyst holder, 15 is a stirring blade, 16 is a conduit, 17 is a conduit, and 18 is a condenser.

In FIG. 3, the reaction tank 13 is a stirring tank fixed-bed reactor loaded with a square pillar holder 14 containing the film-type catalyst. Reactants and/or a product mixture are accommodated in the reaction tank 13, mixed under stirring with a stirring blade 15 driven by a motor, and the temperature can be regulated by external heating. A gaseous primary or secondary amine and a hydrogen gas fed through conduit 16 to the bottom of the reaction tank 13. An unreacted gaseous primary or secondary amine and water are continuously discharged through conduit 17. In the components discharged from the conduit, components such as the alcohol and/or the formed tertiary amine may be contained in the form of vapor or mist, in addition to the components described above, The components are liquified by condenser 18 and returned to the buffer tank 13, and the remaining gaseous components are discharged out of the system. The inside of the reaction system is kept at almost normal pressures.

Production Example 1

Production of a Film-Type Catalyst

Film-type catalyst A having a powdery catalyst fixed with hydroxyethyl cellulose as a binder was prepared in the following manner.

Synthetic zeolite was charged into a 1-L flask, and then a solution of copper nitrate, nickel nitrate and ruthenium chloride dissolved in water in a molar ratio of Cu:Ni:Ru=4:1:0.01, and the mixture was heated under stirring. An aqueous solution of 10 wt % sodium carbonate was added dropwise thereto at 90° C. while the pH of the aqueous solution was controlled in the range of 9 to 10. After aging for 1 hour, the precipitates were filtered, washed with water, dried at 80° C. for 10 hours and calcined at 600° C. for 3 hours to give a powdery catalyst. The contents of metal oxides and synthetic zeolite in the resulting powdery catalyst were 50 wt % and 50 wt %, respectively.

10 parts by weight of hydroxyethyl cellulose (SP-500 manufactured by Daicel Chemical Industries, Ltd.) were added as a binder to 90 parts by weight of the powdery catalyst and mixed with 300 parts by water in a ball mill (media, zirconia ball) to form a coating. A stainless steel foil (thickness 20 µm, 10 cm×30 cm×5 sheets) was used as a substrate, and the coating was applied thereon by a bar coater, dried at 50° C. for 10 minutes and contact-bonded by a roll press machine to fix a film-type catalyst on both sides of the stainless steel foil. As a result of measurement of the thickness of this film-type catalyst with a contact-type film thickness meter (Laser Hologauge LGH-110 manufactured by Mitsutoyo), the thickness of the film-type catalyst on one side, excluding the thickness of the stainless steel foil, was 20 µm. Some of the catalyst specimens thus obtained as the film-type catalyst fixed on both sides of the stainless steel foil were corrugated in a wavy form, stacked alternately with the remaining planar catalyst specimens and wound together. The total weight of the film-type catalyst, excluding the weight of the stainless steel foil, was 7.5 g.

Production Example 2

Production of Film-Type Catalyst

Film-type catalyst B to E having the powdery catalyst fixed with phenol resin as a binder were prepared in the following manner.

Phenol resin (PR-9480 with 58% non-volatiles, manufactured by Sumitomo Bakelite) was added a binder to the powdery catalyst prepared according to Production Example 1, such that the content of non-volatiles in the phenol resin was in the ratio shown in Table 2 below. 2-Butanol was added as solvent thereto such that the solids content (the powdery catalyst and non-volatiles in the phenol resin) became 55%. The mixture was preliminarily mixed by a Disper for 10 minutes, then mixed and dispersed at 1500 rpm for 70 minutes in a basket mill (SS-3 manufactured by ASADA IRON WORKS, Co., Ltd., charged with 800 mL (1900 g) titania beads of 1.4 mm in diameter) to form a coating. A copper foil (thickness 40 µm, 6.5 cm×18 cm×20 sheets) was used as a substrate, and the coating was applied by a bar coater on both sides of the substrate and dried at 150° C. for 30 seconds. Half of the resulting dried catalyst specimens were corrugated in a wavy form, stacked alternately with the remaining planar catalyst specimens and wound together, followed by curing at 150° C. for 90 minutes to fix the film-type catalyst on both sides of the copper foil. The thickness of the resulting film-type catalyst on one side of the copper foil, excluding the thickness of the copper foil, and the total weight of the catalyst excluding the weight of the copper foil were as shown in Table 2.

Production Example 3

Production of a Film-Type Catalyst

Film-type catalyst F for pilot scale reaction, having the powdery catalyst fixed with phenol resin as a binder, was prepared in the following manner.

Phenol resin (PR-9480 with 58% non-volatiles, manufactured by Sumitomo Bakelite) was added as a binder to 100 parts by weight of the powdery catalyst prepared according to Production Example 1, such that the content of non-volatiles in the phenol resin became 47.7 parts by weight. 4-Methyl-2-pentanone was added as solvent thereto such that solids content (the powdery catalyst and non-volatiles in the phenol resin) became 55%. The mixture was preliminarily mixed by a Disper for 10 minutes in a basket mill (SS-3 manufactured by ASADA IRON WORKS, Co., Ltd.) to form a coating. A copper foil (thickness 40 μm, 0.3 m×36 m) was used as a substrate, and the coating was applied by a gravure coater on both sides of the substrate and dried at 150° C. for 30 seconds. The resulting dried specimen was cut into 600 pieces with 30 cm×6 cm, and half of the pieces were corrugated in a wavy form, stacked alternately with the remaining planar catalyst specimens, loaded into a square pillar holder used in a stirring tank fixed-bed reactor, and cured at 150° C. for 90 minutes, to fix the film-type catalyst on both sides of the copper foil. The thickness of the resulting film-type catalyst on one side, excluding the thickness of the copper foil, was 4.9 μm and the total weight of the film-type catalyst excluding the weight of the copper foil was 202 g.

Comparative Production Example 1

Production of a Pellet-Type Catalyst

A pellet-type catalyst having a catalyst active substance fixed by tabletting molding was prepared in the following manner.

The powder before calcination obtained in the step of preparing the powdery catalyst in Production Example 1 was molded into tablets in a cylindrical form of 3 mmφ×3 mm and then calcinated at 600° C. for 3 hours to give a pellet-type catalyst. The bulk density of this pellet-type catalyst was 1.5 g/mL. The thickness of this pellet-type catalyst, based on the outer surface, was expressed as $V_P/S_P$ wherein $V_P$ is volume and $S_P$ is outer surface area, and was 500 μm.

Example 1 and Comparative Example 1

The circulating fixed-bed reaction apparatus shown in FIG. 1 was used to produce N-dodecyl-N,N-dimethylamine from lauryl alcohol and dimethylamine as the starting materials.

Example 1

The film-type catalyst A obtained in Production Example 1 was loaded into the reaction column 1. The volume of the loaded film-type catalyst was 170 mL, and a plurality of flow paths each having a sectional area of about 0.1 cm² running in the axial direction of the reaction column 1 were formed from the film-type catalyst. 600 g lauryl alcohol (KALCOL 20 manufactured by Kao Corporation) was introduced into the buffer tank 2, and while a hydrogen gas was fed at a flow rate of 0.3 L/min. in terms of volume under standard conditions, and circulation of the liquid between the buffer tank 2 and the reaction column 1 was carried out at a flow rate of 2 L/min. The temperature in the reaction column 1 was increased to 210° C., and then dimethylamine was fed to initiate the reaction at 210° C. The amount of dimethylamine fed, which was regulated in accordance with the progress of reaction, was 0.8 g/min. on average during the reaction. Five hours after the reaction was initiated, feed if dimethylamine was terminated, and the whole solution in the buffer tank 2 and the reaction column 1 was discharged. As a result of gas chromatography and quantification by the area percentage method, unreacted lauryl alcohol was 1%, formed N-dodecyl-N,N-dimethylamine was 95%, and N,N-dodecyl-N-methylamine as a byproduct tertiary amine was 4%. N,N,N-Tridodecylamine could not be detected.

Comparative Example 1

250 g of the pellet-type catalyst obtained in Comparative Production Example 1 was loaded into the reaction column 1. The volume of the loaded catalyst was 170 mL. The temperature in the reaction column 1 was increased to 210° C. by the same procedure as in Example 1, and then dimethylamine was fed to imitate the reaction. The amount of dimethylamine fed, which was regulated in accordance with the progress of the reaction, was 0.8 g/min. on average during the reaction. Five hours after the reaction was initiated, feed of dimethylamine was terminated, and the whole solution in the buffer tank 2 and the reaction column 1 was discharged. As a result if gas chromatography in the same manner as in Example 1, unreacted lauryl alcohol was 30%, formed N-dodecyl-N,N-dimethylamine was 60%, N,N-didodecyl-N-methylamine as a byproduct tertiary amine was 5%, and others were 5%. That is, the rate of reaction was lower than in Example 1, the amount of the byproduct was high and the yield was low, as shown in table 1.

Examples 2 to 5

The bubbling tank reaction apparatus shown in FIG. 2 was used to produce N-dodecyl-N,N-dimethylamine from lauryl alcohol and dimethylamine as the starting materials.

Example 2

The film-type catalyst B obtained in Production Example 2 was loaded into the reaction tank 7. The volume of the loaded film-type catalyst was 276 mL, and a plurality of flow paths each having a sectional area of about 0.1 cm² running in the vertical direction of the reaction tank 7 were formed from the film-type catalyst. 1000 g lauryl alcohol (KALCOL 20 manufactured by Kao Corporation) was introduced into the reaction tank 7, and while a hydrogen gas was fed at a flow rate of 0.33 L/min. in terms of volume under standard conditions, the temperature in the reaction tank 7 was increased to 220° C. and then dimethylamine was fed to initiate the reaction to 220° C. The amount of dimethylamine fed, which was regulated in accordance with the progress of the reaction, was 300 g in total. The solution in the reaction tank 7 was sampled with time and analyzed by gas chromatography to quantify its components by the area percentage method. When unreacted lauryl alcohol was 1%, feed of dimethylamine was terminated to finish the reaction, and the whole solution was discharged from the reaction tank 7. The reaction activity α [/Hr/%-active substance] per unit weight of the catalyst active substance was 3.5 [/Hr/%-active substance] as determined from the following formula (1) by using the concentration C (%) of unreacted alcohol 0.5 hour before conclusion of the reaction, the weight w (g) of the film-type catalyst, and the amount p [parts by weight based on 100 parts by weight of the powdery catalyst] of phenol resin non-volatiles incorporated into the film-type catalyst.

$$\alpha = \frac{\ln C}{0.5\left(\frac{w\left(\frac{100}{100+p}\right)}{1000} \times 100\right)} \quad (1)$$

As a result of quantitative analysis of the discharged solution by gas chromatography, formed N-dodecyl-N,N-dimethylamine was 92.1%, and N,N-didodecyl-N-methylamine as a byproduct tertiary amine was 5.7%. N,N,N-Tridecylamnine could not be detected. The whole volume of the discharged solution was filtered through a membrane filter (made of PTFE with a pore diameter of 2.0 μm), and solids remaining on the membrane filter were washed with acetone, dried and weighed as fine powders generated from the film-type catalyst, to determine the amount of the generated fine powders. The amount of the generated fine powders was 0.13 g.

Measurement of the Pore Volume

The volume of pores with a diameter in the range of 10 μm to 5 μm was measured with a mercury porosimetry measuring instrument (Pore Sizer 9320) manufactured by Shimad Z u Corporation. From the measured pore volume V [mL] and the substance surface area S [m$^2$] of the film-type catalyst used in measurement, the pore volume $V_S$ [mL/m$^2$] per unit surface area of the substrate in the present invention is calculated according to the equation: $V_S$=V/S. The film-type catalyst sample, for example when fixed on both sides of a planar substrate of 20 mm+20 mm in size, has a surface area S of 8×10−4 m$^2$, or the film-type catalyst sample when fixed on one side of a planar substrate having the same size as above has a surface area S of 4×10−4 m$^2$. As a result of measurement, the pore volume $V_S$ was 2.9 mL/m$^2$.

Examples 3 to 5

N-Dodecyl-N,N-dimethylamine was produced from lauryl alcohol and dimethylamine as the starting material under the conditions shown in Table 2 by the same method as in Example 2. The reaction activity per unit weight of the catalyst active substance, the result of quantification of the discharged solution by gas chromatography, the amount of the fine powders generated from the film-type catalyst, and the pore volume were as shown in Table 2.

Example 6

Using the stirring tank reaction apparatus shown in FIG. 3, N-dodecyl-N,N-dimethylamine was produced from lauryl alcohol and dimethylamine as the starting material.

The film-type catalyst F obtained in Production Example 3 was loaded into the square pillar holder 14 and fit in the reaction tank 13. The volume of the loaded film-type catalyst was 10.4 L, and a plurality of flow paths each having a sectional area of about 0.1 cm$^2$ running in the vertical direction of the reaction tank 13 were formed from the film-typed catalyst. 46.1 kg lauryl alcohol (KALCOL 20 manufactured by Kao Corporation) was introduced into the reaction tank 13, and while a hydrogen gas was fed at a flow rate of 25 L/min. in terms of volume under standard conditions, the solutions was stirred at a revolution number of 550 rpm with a concave turbine blade, the temperature in the reaction tank 13 was increased to 225° C., and then dimethylamine was fed to initiate the reaction at 225° C. The amount of dimethylamine fed, which was regulated in accordance with the progress of the reaction, was 50 g/min, on average during the reaction. 4.8 hours after the reaction was initiated, feed of dimethylamine was terminated, and the whole of the solution was discharged from the reaction tank 13. As a result of gas chromatography and quantification by the area percentage method, unreacted lauryl alcohol was 1%, formed N-dodecyl-N,N-dimethylamine was 92.4%, and N,N-didodecyl N-methylamine as a byproduct tertiary amine was 5.1%. N,N,N-Tridecylamine could not be detected.

TABLE 1

|  |  | Example 1 | Comparative example 1 |
| --- | --- | --- | --- |
| Catalyst |  | Film-type catalyst A | Pellet-type catalyst |
| Catalyst active substance |  | Cu—Ni—Ru ternary element powdery catalyst | |
| Compounding amount | (parts by weight) | 90 | 100 |
| Binder |  | Hydroxyethyl cellulose | — |
| Compounding amount | (parts by weight) | 10 | — |
| Weight (excluding the substrate foil) | (g) | 7.5 | 250 |
| Film thickness | (μm) | 20 | 500* |
| Reaction time | (Hr) | 5 | 5 |
| Reaction activity | (/Hr/%) | 1.2 | 0.006** |
| N-Dodecyl-N,N-dimethylamine | (wt %) | 95 | 60 |
| N,N-Didodecyl-N-methylamine | (wt %) | 4 | 5 |
| Lauryl alcohol | (wt %) | 1 | 30 |

*The film thickness of the pellet-type catalyst is thickness based on outer surface.

**Because 30% unreacted starting alcohol remained; the reaction activity was calculated by the formula (1) wherein lnC was replaced by lnC—ln30 and p was 0.

TABLE 2

|  |  | Example 2 | Example 3 | Example 4 | Example 5 |
| --- | --- | --- | --- | --- | --- |
| Film-type catalyst |  | B | C | D | E |
| Catalyst active substance |  | Cu—Ni—Ru ternary element powdery catalyst | | | |
| Compounding amount | (Parts by weight) | 100 | 100 | 100 | 100 |
| Phenol resin |  | PR-9480 (58% non-volatiles) | | | |
| Amount of non-volatiles compounded | (parts by weight) | 11.1 | 25 | 53.8 | 47.7 |
| Weight (excluding copper foil) | (g) | 5.0 | 5.1 | 13.7 | 5.6 |
| Film thickness | (μm) | 5.3 | 5.2 | 14.5 | 6.2 |
| Pore volume | (mL/m$^2$) | 2.9 | 2.1 | 3.3 | 1.9 |
| Reaction activity | (/Hr/%) | 3.5 | 3.1 | 1.7 | 3.5 |
| N-Dodecyl-N,N-dimethylamine | (wt %) | 92.1 | 92.5 | 86.0 | 93.7 |
| N,N-Didodecyl-N-methylamine | (wt %) | 5.7 | 5.8 | 10.6 | 4.7 |
| Amount of fine powders generated | (g) | 0.13 | 0.05 | 0.04 | 0.03 |

The invention claimed is:

1. A film-type catalyst for production of a tertiary amine, which is used in producing a tertiary amine from an alcohol and a primary or secondary amine as the starting material;
wherein said film-type catalyst comprises catalyst particles bound to one another via a synthetic resin as a binder;
wherein said particles form a three-dimensional network structure via the binder on a substrate;
wherein said film-type catalyst has a thickness of 500 μm or less and a pore volume of not less than 0.5 mL/m$^2$, whereby a diffusion rate in the film-type catalyst layer is increased due to said three-dimensional network structure, and the mass transfer between the inside and outside of the film-type catalyst can be promoted thereby utilizing the whole of the catalyst and simultaneously suppressing the excessive reaction of an intermediate reaction product in the inside of the catalyst;

wherein the inside of the catalyst is a site of reaction for producing said tertiary amine; and wherein the synthetic resin is in an amount of 20 to 80 parts by weight relative to 100 parts by weight of a powdery catalyst active substance on the basis of the starting material.

2. The film-type catalyst according to claim 1, which has a thickness of 100 μm or less.

3. The film-type catalyst according to claim 1 or 2, which comprises copper.

4. The film-type catalyst according to claim 1, which is fixed on the surface of the substrate.

5. The film-type catalyst according to claim 1, which has a pore volume of 0.5 to 30 mL/m$^2$.

6. The film-type catalyst according to claim 5, wherein the synthetic resin comprises thermosetting resin.

7. The film-type catalyst according to claim 5 or 6, wherein the synthetic resin comprises phenol resin.

8. The film-type catalyst according to claim 4, wherein the substrate is a metal foil.

9. The film-type catalyst according to claim 4, wherein the substrate is a honeycomb structure.

10. A process for producing a tertiary amine, which comprises a step of reacting an alcohol with a primary or secondary amine inside a film-type catalyst having a thickness of 500 μm or less and a pore volume of not less than 0.5 mL/m$^2$, wherein said film-type catalyst comprises catalyst particles bound to one another via a synthetic resin as a binder;

wherein said particles form a three-dimensional network structure via the binder on a substrate;

whereby a diffusion rate in the film-type catalyst layer is increased due to said three-dimensional network structure, and the mass transfer between the inside and outside of the film-type catalyst can be promoted thereby utilizing the whole of the catalyst and simultaneously suppressing the excessive reaction of an intermediate reaction product in the inside of the catalyst; and wherein the synthetic resin is in an amount of 20 to 80 parts by weight relative to 100 parts by weight of a powdery catalyst active substance on the basis of the starting material.

11. The process according to claim 10, wherein the film-type catalyst has a thickness of 100 μm or less.

12. The process according to claim 10, wherein the film-type catalyst comprises copper.

13. The process according to claim 10, wherein the film-type catalyst is fixed on the surface of the substrate.

14. The process according to claim 13, wherein the substrate is a metal foil.

15. The process according to claim 13, wherein the substrate is a honeycomb structure.

* * * * *